US007842502B2

(12) United States Patent
Luyten et al.

(10) Patent No.: US 7,842,502 B2
(45) Date of Patent: Nov. 30, 2010

(54) USE OF CXCL6 CHEMOKINE FOR INDUCING PRECURSOR CELLS INTO CHONDROCYTES

(75) Inventors: Frank Luyten, Kraainem (BE); Cosimo De Bari, Aberdeen (GB); Francesco Dell'Accio, Bromley (GB)

(73) Assignee: Tigenix N.V., Leuven (BE)

( * ) Notice: Subject to any disclaimer, the term of this patent is extended or adjusted under 35 U.S.C. 154(b) by 0 days.

(21) Appl. No.: 12/345,369

(22) Filed: Dec. 29, 2008

(65) Prior Publication Data

US 2009/0117652 A1 May 7, 2009

Related U.S. Application Data

(62) Division of application No. 10/595,072, filed as application No. PCT/BE2004/000117 on Aug. 12, 2004, now Pat. No. 7,485,310.

(60) Provisional application No. 60/494,516, filed on Aug. 12, 2003.

(51) Int. Cl.
*C12N 5/0775* (2010.01)
*C07K 14/475* (2006.01)
*A61K 38/18* (2006.01)

(52) U.S. Cl. ............................ 435/377; 435/4; 530/350; 530/399

(58) Field of Classification Search ........................ None
See application file for complete search history.

(56) References Cited

U.S. PATENT DOCUMENTS

| | | | |
|---|---|---|---|
| 5,786,217 | A | 7/1998 | Tubo et al. |
| 5,840,524 | A | 11/1998 | Van Damme et al. |
| 6,090,625 | A | 7/2000 | Abuljadayfl et al. |
| 6,410,268 | B1 | 6/2002 | Ni et al. |
| 6,413,511 | B1 | 7/2002 | Glorioso et al. |
| 2002/0123483 | A1 | 9/2002 | Saxena et al. |
| 2003/0224345 | A1* | 12/2003 | West et al. ............ 435/4 |
| 2005/0019865 | A1 | 1/2005 | Kihm et al. |
| 2006/0153817 | A1 | 7/2006 | Kihm et al. |
| 2006/0154366 | A1 | 7/2006 | Brown et al. |
| 2006/0154367 | A1 | 7/2006 | Kihm et al. |

FOREIGN PATENT DOCUMENTS

EP 1 312 614 A1 5/2003

RU 2 177 996 1/2002

OTHER PUBLICATIONS

Sell, S. (ed.) Stem Cells Handbook. 2004. New Jersey: Human Press, pp. 1-18 and table of contents.*
Phillips, A.. The challenge of gene therapy and DNA delivery. J Pharm Pharmacology 53:1169-1174, 2001.*
Rubanyi et al. The future of human gene therapy. Mol Aspects Med 22: 113-142, 2001.*
Juengst, E.T. What next for human gene therapy? Brit Med J 326: 1410-1411, 2003.*
Lin et al. The Chondrocyte: biology and clinical application. Tissue Engineering 12(7): 1971-1984, 2006.*
Haringman et al., "Chemokines in Joint Disease: The Key to Inflammation?"*Ann Rheum. Dis.* 63(10):1186-1194 (2004).
Imhof et al., "Subchondral Bone and Cartilage Disease: A Rediscovered Functional Unit," *Invest. Radiol.* 35(10):581-588 (2000).
Lindahl et al., "Cartilage Repair with Chondrocytes: Clinical and Cellular Aspects" in *Tissue Engineering of Cartilage and Bone*, Novartis Foundation Symposium 249 UK: John Wiley and Sons Ltd., pp. 175-189 (2003).
Meyer and Wiesmann, *Bone and Cartilage*, Germany: Springer, pp. 7-46 (2006).
Wuyts et al., "Characterization of Synthetic Human Granulocyte Chemotactic Protein 2: Usage of Chemokine Receptors CXCR1 and CXCR2 and In Vivo Inflammatory Properties," *Biochem.* 36(9):2716-2723 (1997).
Wuyts et al., "The CXC Chemokine GCP-2/CXCL6 is Predominantly Induced in Mesenchymal Cells by Interleukin-1β and is Down-Regulated by Interfernon-γ: Comparison with Interleukin-8/CXCL8," *Lab. Invest.* 83(1):23-34 (2003).
International Preliminary Report on Patentability for PCT/BE2004/000117, mailed Dec. 5, 2005.
International Search Report for PCT/BE2004/000117, mailed Feb. 2, 2005.
Response to the Written Opinion for PCT/BE2004/000117, mailed Jun. 1, 2005.
Translation of Office Action mailed Jul. 9, 2008 in connection with Russian Patent Application No. 2006107536/(008178).
Written Opinion of the International Searching Authority for PCT/BE2004/000117, mailed Feb. 2, 2005.
Office Action for Japanese Application No. 2006-522851, dated Jun. 8, 2010.
English language summary dated Jun. 10, 2010 of Office Action for Japanese Application No. 2006-522851, dated Jun. 8, 2010 (2 pages). (Redacted).

* cited by examiner

*Primary Examiner*—Bridget E Bunner
(74) *Attorney, Agent, or Firm*—Clark & Elbing LLP

(57) ABSTRACT

The present invention disclosed the expression of CXCL6 by cells which are able to form stable cartilage. The invention describes the use of these cells and of CXCL6 to promote cartilage (and underlying bone) formation e.g. in the repair of cartilage or osteochondral defects. The invention further describes the use of chemokines in the modulation of progenitor cell differentiation.

2 Claims, 2 Drawing Sheets

USE OF CXCL6 CHEMOKINE FOR INDUCING PRECURSOR CELLS INTO CHONDROCYTES

CROSS-REFERENCE TO RELATED APPLICATIONS

This application is a divisional of U.S. patent application Ser. No. 10/595,072, filed May 9, 2006, now U.S. Pat. No. 7,485,310, which is the U.S. National Stage of International Application PCT/BE04/00117, filed Aug. 12, 2004, which in turn claims the benefit of the filing date of U.S. Provisional Application Ser. No. 60/494,516, filed Aug. 12, 2003.

FIELD OF THE INVENTION

The present invention relates to the formation of cartilage and bone in vitro and in vivo and especially to the repair of cartilage or osteochondral defects or to the formation of bone or cartilage in cosmetic surgery. More particularly it relates to the repair and prevention of joint defects, such as occurring in osteoarthritis. The invention further relates to modulation of differentiation of progenitor cells into chondrogenic cells.

BACKGROUND OF THE INVENTION

Chemokines are a group of small (approximately 8 to 14 kD), mostly basic, structurally related molecules that regulate cell trafficking of various types of leukocytes through interactions with a subset of 7-transmembrane, G protein-coupled receptors. Chemokines play fundamental roles in the development, homeostasis and function of the immune system, and have effects on cells of the central nervous system as well as on endothelial cells that are involved in angiogenesis or angiostasis. Chemokines are divided into 2 major subfamilies, CXC and CC, based on the arrangement of the first 2 of the 4 conserved cysteine residues which occur in chemokine protein sequences; the 2 cysteines are separated by a single amino acid in CXC chemokines and are adjacent in CC chemokines. CXC chemokines are further subdivided into ELR and non-ELR types based on the presence or absence of a glu-leu-arg sequence (ELR motif) adjacent and N-terminal to the CXC motif. A new classification system which groups the different chemokines was presented by Zlotnik and Yoshie (2000, *Immunity* 12, 121-127) and is presented in Table 1.

TABLE 1 classification of CXC chemokines and chemokine receptors
(From Zlotnik and Yoshie cited above).
CXC Chemokine Family

| Systematic Name | Human Chromosome | Human Ligand | Mouse Ligand | Chemokine Receptor(s) |
|---|---|---|---|---|
| CXCL1 | 4q12-q13 | GROalpha/MGSA-alpha | GRO/KC? | CXCR2 > CXCR1 |
| CXCL2 | 4q12-q13 | GRObeta/MGSA-beta | GRO/KC? | CXCR2 |
| CXCL3 | 4q12-q13 | GROgamma/MGSA-gamma | GRO/KC? | CXCR2 |
| CXCL4 | 4q12-q13 | PF4 | PF4 | Unknown |
| CXCL5 | 4q12-q13 | ENA-78 | LIX? | CXCR2 |
| CXCL6 | 4q12-q13 | GCP-2 | CKa-3 | CXCR1, CXCR2 |
| CXCL7 | 4q12-q13 | NAP-2 | Unknown | CXCR2 |
| CXCL8 | 4q12-q13 | IL-8 | Unknown | CXCR1, CXCR2 |
| CXCL9 | 4q21.21 | Mig | Mig | CXCR3 |
| CXCL10 | 4q21.21 | IP-10 | IP-10 | CXCR3 |
| CXCL11 | 4q21.21 | I-TAC | Unknown | CXCR3 |
| CXCL12 | 10q11.1 | SDF-1alpha/beta | SDF-1 | CXCR4 |
| CXCL13 | 4q21 | BLC/BCA-1 | BLC/BCA-1 | CXCR5 |
| CXCL14 | Unknown | BRAK/bolekine | BRAK | Unknown |
| CXCL15 | Unknown | Unknown | Lungkine | Unknown |

The human chemokine GCP 2 was originally discovered as a protein which was expressed in minute amounts together with Interleukin 8 (IL-8) by stimulated human osteosarcoma cells (Proost et al. (1993) *Biochemistry* 32, 10170-10177). The human gene for GCP-2 encodes a protein of 114 amino acids.

GCP-2, previously named 'SCYB6', and according to most recent terminology 'CXCL6', shows the strongest sequence similarity in coding and noncoding sequence to CXCL5 (SCYB5/ENA-78 (Epithelial cell-derived Neutrophil Attractant 78)).

In humans and cows the CXCL6 protein occurs in a number of N-terminally truncated forms which seem to have no different activity in a standard in vitro migration assay (Proost et al. (1993) cited above). Up to 28 N-terminally and/or C-terminally cleaved versions of murine CXCL6 were isolated from fibroblasts and epithelial cells (Wuyts et al. (1999) *J. Immunol.* 163, 6155-6163; Van Damme et al. (1997) *J Leukoc Biol* 6, 563-569). These N-terminally truncated versions of murine CXCL6 show dramatic differences in specific chemotactic potency towards both human and murine neutrophils in vitro and in vivo. CXCL6 is reported to be a specific granulocyte attractant having no chemotactic effect on monocytes (Van Damme et al. (1997) cited above).

As its name indicates CXCL6 is a CXC chemokine. It belongs to the subgroup of neutrophil activating chemokines acting through CXCR1 which are characterized by the N-terminally located Glu-Leu-Arg sequence (ELR motif). Together with IL-8, CXCL6 is the only ELR-containing chemokine that has a basic amino acid at the sixth position after the second cysteine of the CXC motif. Wolf et al. ((1998) *Eur. J. immunol.* 28, 164-170) have shown that this basic amino acid is an important determinant for CXCR1 activation. Wuyts et al. ((1997) cited above) further demonstrated that CXCL6 binds to both CXCR1 and CXCR2 receptors.

Chemokines in general have been connected to cartilage degradation in the context of the inflammatory reaction observed in rheumatoid arthritis. Borzi et al. ((1999) *Febs Left.* 455, 235-242) and Pulsatelli et al. ((1999) *J. Rheumatol.* 26, 1992-2001) describe the expression of IL-8, Gro-alpha, MCP-1, RANTES, MIP-1alpha and MIP1beta in chondrocytes obtained from normal individuals, osteoarthritis (OA) and rheumatoid arthritis (RA) patients. Borzi et al. ((2002) *Arthritis Rheum.* 46, 3201-3211) suggest the existence of a novel catabolic pathway primed by chemokines and their receptors that leads to the breakdown of cartilage matrix components. The upregulation of chemokines, according to these authors, is related to the pathogenesis and persistence of the joint disease. Votta et al. ((2000) *J Cell Physiol.* 183, 196-207) suggest that the CC chemokine Ckbeta 8 plays a role in the recruitment of osteoclast precursors to sites of bone resorption. Osteoblasts on the other hand do not respond to this chemokine. Alaaeddine et al. ((2001) *Arthritis Rheum.* 44, 1633-1643) studied the expression of the chemokine RANTES (a member of the CC family) and its receptors in normal and OA cartilage and assigned a pathogenetic activity to this chemokine. Kanbe et al. ((2002) *Arthritis Rheum.* 46, 130-137) have suggested a role for the CXC chemokine SDF-1 in synovial cell mediated degradation of cartilage matrix in RA and OA. Wuyts et al. ((2003) *Lab Invest* 83, 23-34) demonstrated that inflammatory cytokines such as IL-1 induce CXCL6 expression in chondrocytes, although this expression level is about 100 times less than IL-8.

Silvestri et al. ((2003) *Rheumatology* 42, 14-18) describe the expression of chemokine receptors, but not of the chemokines themselves, in inflammatory arthritis and osteoarthritis. It is postulated that the activity of chemokines tilts the balance of cartilage homeostasis towards degradation. EP 08044865 suggests the use of CXCL6 as a medicament for inflammatory conditions, while U.S. Pat. No. 6,410,268 indicates the possible use of GCP2-antagonists in the treatment of inflammatory diseases such as RA. The latter furthermore suggests the use of GCP-2 to stimulate wound-healing in the treatment of fibrotic diseases such as OA.

A role of chemokines in the migration of cell types which are unrelated to leukocytes has recently emerged. As cited above, a chemotactic effect of Ckbeta 8 on osteoclast precursors has been described (Votta et al. (2000) *J Cell Physiol.* 183, 196-207). Doitsidou et al. ((2003) *Cell* 11, 647-59) and Wright et al. ((2002) *J Exp Med.* 195, 1145-1154) demonstrate the role of SDF-1 and its receptor CXCR4 in the migration of primordial germ cells and hematopoietic stem cells respectively. King et al. ((2000) *Blood* 97, 1534-1542 and (2001) *J. Immunol.* 164, 3774-3782) describe a dramatic increase in hematopoietic activity upon amino-terminal truncation of CXCL2 (GroBeta) and demonstrate that this truncated version can mobilize hematopoietic stem cells. U.S. Pat. No. 6,410,268 speculates on a possible role in mobilization of stem cells using CXCL6, in particular of bone marrow stem cells, which could be applied in the treatment of cancer and leukemia.

SUMMARY OF THE INVENTION

The present invention relates to the involvement of chemokine CXCL6 in the formation of bone or cartilage in vitro or in vivo, e.g. in cosmetic surgery, and particularly to the repair or prevention of cartilage or osteochondral defects, more particularly joint surface defects. More particularly, it relates to the use of CXCL6 and cell populations with chondrogenic properties which express the chemokine CXCL6 in the formation in vitro or in vivo of cartilage or bone, e.g. in cosmetic surgery or in the treatment of joint surface defects, such as osteoarthritis.

The present invention is based on the finding that the differentiation of stem cells into cartilage-forming cells is severely reduced or blocked by antibodies against the chemokine receptor CXCR1, and to a lesser extent by antibodies against the chemokine receptor CXCR2, and particularly by the blocking of both CXCR1 and 2, indicating that chemokines and one or more chemokine signalling pathways are involved in the differentiation to cartilage or bone producing cells. Furthermore it was found that cell populations that have the potential to form stable cartilage, reproducibly express the chemokine CXCL6 as a positive marker. A further finding of the present invention is that CXCL6 is involved in the restoration of osteochondral defects. Thus, contrary to the involvement of chemokines in cartilage degradation as described in the prior art, the present invention relates to the use of CXCL6 and CXCL6 expressing cells in the formation of cartilage or bone in vitro or in vivo and in the repair of cartilage or osteochondral defects.

According to the present invention the use of chemokine CXCL6 is described in the treatment or prevention of a cartilage or osteochondral defect, a defect of joint-related tissues and defects of other tissues of a fibrocartilage nature such as intervertebral discs, as well as in the formation of bone or cartilage in other indications, e.g. cosmetic surgery. More particularly, the present invention relates to the stimulation of hyaline cartilage (and underlying bone) formation in a cartilage or osteochondral defect using CXCL6.

A first aspect of the present invention describes CXCL6 for the preparation of a medicament for the promotion of bone or cartilage formation in vivo or in vitro. In particular the present invention describes CXCL6 for the prevention or treatment of a cartilage or osteochondral defect. The source of CXCL6 according to this aspect of the invention can be either natural, recombinant or synthetic. Accordingly, the present invention describes a composition comprising CXCL6 for use in the promotion of bone or cartilage formation in vivo or in vitro. In particular a composition is described comprising CXCL6 for the prevention or treatment of a cartilage or osteochondral defect. According to a particular embodiment of this aspect of the invention, such a composition comprising CXCL6 can further comprise chondrogenic cells, i.e., cells capable of producing stable hyaline cartilage, and/or precursor cells of chondrogenic cells. Alternatively, CXCL6 is administered through gene therapy.

According to a second aspect of the invention, the use of cells expressing CXCL6, more particularly chondrogenic cells expressing CXCL6 is described to promote formation of bone and/or cartilage in vivo or in vitro. In particular, the use of cells expressing CXCL6, more particularly chondrogenic cells expressing CXCL6 is described in the treatment or prevention of a cartilage or osteochondral defect. Accordingly, the present invention describes a composition comprising cells, more particularly chondrogenic cells, expressing CXCL6 for use as a medicament for the promotion of bone or cartilage formation in vivo, more particularly for use in the prevention and treatment of a cartilage or osteochondral defect or for the preparation of a medicament for the prevention or treatment of a cartilage or osteochondral defect.

According to a particular embodiment of the present invention, CXCL6 expressing chondrogenic cells are isolated from connective tissue, more particularly from the synovial membrane.

Alternatively, according to another aspect of the invention, CXCL6 expressing cells are obtained by introducing into suitable cells, more particularly connective tissue cells, a foreign DNA encoding CXCL6 under control of a suitable promoter.

According to a particular aspect of the present invention, cells expressing CXCL6 are embedded in a matrix for use in the promotion of bone or cartilage formation in vivo or in vitro or in the treatment of osteochondral defects.

Alternatively, according to another aspect of the present invention, pharmaceutical compositions comprising one or more compounds capable of inducing the endogenous expression of CXCL6 by chondrogenic cells are used for the promotion of the formation of cartilage or bone in vivo and particularly in the treatment or prevention of cartilage or osteochondral defects.

The present invention relates to the use of CXCL6 and/or CXCL6 expressing cells, or compounds inducing endogenous CXCL6 expression, optionally in combination with chondrogenic cells or chondrogenic precursor cells for the promotion of bone or cartilage formation in vitro or in vivo or in the treatment or prevention of cartilage or osteochondral defects. According to a particular aspect of the present invention the CXCL6 and/or CXCL6-expressing cells (or DNA) or compounds inducing endogenous CXCL6 expression are administered locally for the promotion of cartilage or bone formation or for the treatment of cartilage or osteochondral defects, more particularly joint surface defects. According to another particular aspect of the present invention, such a joint surface defect is not related to inflammation, such as a joint surface defect observed in osteoarthritis.

According to yet another aspect of the present invention, expression of CXCL6 is used as a marker for chondrocyte phenotypic stability, i.e. to monitor the ability of a chondrocyte cell population to produce stable hyaline cartilage in vivo. Thus, according to this aspect of the invention expression of CXCL6 can be used as a marker to identify chondrogenic cell populations, suitable for use in the promotion of cartilage or bone formation in vivo or in vitro or in the treatment and prevention of cartilage defects.

According to yet another aspect of the present invention, one or more chemokine pathways are used to modulate the differentiation of progenitor cells. Thus, the invention describes the use of ligands or inhibitors for the CXCR1 and/or CXCR2 receptors for the modulation of differentiation of progenitor cells into cartilage and bone-producing cells. More specifically, according to the present invention ligands of either or both of the CXCR1-2 receptors are used to stimulate differentiation into cartilage-producing cells, while inhibitors are used to inhibit differentiation into cartilage producing cells.

A particular embodiment is the stimulation of differentiation by a chemokine binding to the CXCR1 (and/or CXCR2) receptor. More particularly, CXCL6 is used to induce the differentiation of progenitor cells into cartilage and/or bone forming cells. Thus, according to this embodiment of the invention CXCL6 is used to stimulate differentiation of progenitor cells in vitro or in vivo and is optionally administered to an osteochondral defect in combination with precursor cells of chondrogenic cells ('chondrogenic precursor cells').

The invention further relates to an in vitro method of inducing or restoring differentiation of a precursor cell population into chondrocytes, said method comprising the step of administering CXCL6 to such precursor cell population.

The use of CXCL6 is indicated to maintain a or restore a stable chondrogenic population, i.e. a population capable of producing stable hyaline cartilage.

The invention also relates to a method for the detection of a compound or mixture of compounds (such as e.g. a plant extract) for the promotion of cartilage and bone promotion in vivo, said compound or mixture of compounds modulating CXCL6 signalling, and said method comprising the steps of contacting a cell population with a candidate compound or mixture of compounds and determining a modified expression level of CXCL6. The cell population can be any cell type which expresses CXCL or which is adapted in order to measure the expression of CXCL6 levels, more particularly the cell population is being selected from the group consisting of chondrocytes, chondrocytes precursors and chondrocyte progenitors. Optionally the method comprising an additional step of determining one or more morphological or molecular parameters of said chondrocyte, chondrocytes precursor or chondrocyte progenitor cell population.

DETAILED DESCRIPTION

As used herein 'CXCL6' relates to a chemokine also referred to as SCYB6 (small inducible cytokine subfamily B, member 6) or GCP-2 (Granulocyte Chemotactic Protein 2)(Genbank numbers NP 002984 and P80162). It includes both the full-length protein and modified versions such as N-terminally and/or C-terminally truncated versions of the protein, with the restriction that said modified proteins retain the chemotactic activity towards cells beneficial for cartilage (and adjacent bone) repair, such as chondrocytes and chondrocyte precursor cells. The truncations can be, but are not restricted to those of naturally occurring splice variants and/or processed forms. Possible N- and/or C-terminal truncation include those described by Wuyts et al. ((1999) *J. Immunol.* 163, 6155-6163). CXCL6 modifications according to the present invention also include those wherein the ELR motif has been modified or deleted up to the level where no leukocyte attraction occurs and those modified versions wherein the basic amino acid at the sixth position after the second cystein of the CXC motif has been modified. CXCL6 as used herein relates to natural (e.g. as obtained from the supernatant of cells which naturally express CXCL6), recombinant and synthetic versions of the chemokine. A preferred embodiment of CXCL6 is the 75 amino acid CXCL6 as described by Wuyts et al. ((1997) cited above). CXCL6 as referred to in the present invention can further include fusion products of CXCL6 or a biologically active part thereof with optionally cleavable sites, with tags or domains for detection or purification.

Means to obtain or produce CXCL6 are described in the art. Examples thereof are summarized hereafter, the cited publications being incorporated herein by reference. Mammalian GCP-2 can be obtained by culturing a mammalian cells sample which is stimulated to produce cytokines, and purification of CXCL6 from the medium. A four-step isolation procedure to purify amongst other chemokines CXCL6 from conditioned medium of transfected cells is presented in (Wuyts et al. (1997) *Methods Enzymol* 287, 13-33). Recombinant DNA techniques known to the skilled person at the time of the invention, such as expression in prokaryotic and eukaryotic expression-systems (yeast, baculovirus, mammalian cells) can be used for the production of CXCL6. Froyen et al. ((1997) *Eur J Biochem* 243, 762-769) describe expression of CXCL6 into the periplasm of *E. Coli*. The expression of CXCL6 in COS cells and in a Baculovirus expression system is described in U.S. Pat. No. 6,410,268. Biologically active CXCL6 has also been obtained by chemical synthesis, followed by introduction of disulphide bridges (Wuyts et al. (1997) cited above). Methods for obtaining CXCL6 are furthermore described in EP 0804486.

The term 'Chemokine' as used herein relates to a small polypeptide with a molecular weight of about 8,000 to 14,000, which is able to direct the movement of cells such as leukocytes (as reviewed by Zlotnik and Yoshie (2000) cited above).

'Chemotaxis' refers to the movement of cells in response to a chemical compound (i.e. chemokine) whereby the cells are either attracted (positive chemotaxis) or repelled (negative chemotaxis) by said chemical compound. Different methods to measure chemotaxis have been described in the art. Chemotaxis can be measured under agarose as described for example by Nelson ((1975) *J. Immunol.* 115, 1650-1656), whereby the test sample (ie chemotactic compound) is introduced into the agarose and potentially responsive cells are introduced at a certain distance therefrom. The chemotactic effect of the test sample is determined by microscopically measuring the migration distance of the cells in the agarose. Negative (ie not containing a chemoattractant) and positive (e.g. fMLP, a known chemoattractant) controls are included to eliminate false positives and negatives, respectively. Alternatively, chemotactic activity can be measured using a microchamber (such as described by Falk et al. ((1980) *J Immunol Methods.* 33, 239-247). The lower compartment of the microchamber is loaded with a test sample, while the upper compartment is filled with a medium containing cells. The lower and upper compartments are separated by a 5 μm pore-size polycarbonate membrane. After an incubation period, the membrane is removed, fixed and stained, and the chemotactic effect of the test sample is determined by scoring the number of cells that have migrated through the membrane. Again positive and negative controls are included. Other methods for measuring the chemotactic activity of compounds, such as in vivo injection are described in the art.

'Chemoattractant' refers to a chemical compound which induces the migration of a cell towards said chemical compound.

A 'responsive cell' as used herein refers to a cell which is either attracted or repelled by a chemokine. More particularly, in the context of the present invention, a responsive cell is a cell that is attracted or repelled by CXCL6.

'Stable hyaline cartilage' as used herein refers to cartilage without signs of vascular infiltration (i.e. devoid of vascularization) fibrous tissue or endochondral bone formation.

'Phenotypic stability' refers to the maintenance of the ability of a cell to organize or reorganize, in vivo, the structure of a specific tissue, either the original tissue where the cells were taken from, or a different tissue the cells have been forced to form under specific conditions.

A phenotypically stable chondrocyte, refers to a chondrocyte which retains its ability to form stable hyaline cartilage (also referred to as 'chondrocyte stability'). A phenotypically stable chondrocyte cell suspension or population refers to the ability of a cell suspension or population to produce stable hyaline cartilage in vivo, e.g., in an animal model for cartilage production. Preferably the model comprises injection of a cell suspension in a mammal (in vivo) such as an immune-deficient mouse, and evaluation, in a time frame of 3 weeks of the formation of a cartilage implant, whereby stable hyaline cartilage is formed when the cartilage implant shows no signs of vascular invasion or endochondral bone formation. An example of such an assay is described in WO 01/24833, incorporated herein by reference.

'Chondrogenic' refers to the capacity to promote or stimulate cartilage growth. When relating to a molecule, chondrogenic as used herein refers to the ability of the substance, when applied to cells such as chondrocytes and to cells which themselves differentiate into chondrocytes, to directly or indirectly promote or stimulate cartilage formation by these cells.

'Chondrogenic cells' are cells capable of producing stable hyaline cartilage.

'Connective tissue' as used herein refers to any of a number of structural tissues in the body of a mammal including bone, cartilage, ligament, tendon, meniscus, dermis, hyperdermis, muscle, fatty tissue, joint capsule.

A 'precursor cell' as used herein refers to a cell having the capacity of undergoing differentiation to perform a specific function. More specifically, in the context of the present invention, a precursor cell of a chondrogenic cell is a precursor cell capable of undergoing differentiation into a cell capable of producing stable hyaline cartilage (also referred to as 'chondrogenic precursor cell').

A 'cell population expressing CXCL6' as used herein refers to a cell-population wherein at least 70%, preferably 80%, particularly 85%, more particularly 90%, or optionally 95% or more of the cells expresses CXCL6. Cells expressing CXCL6 within such a population can be identified by methods is known in the art such as Fluorescence Automated Cell Sorting (FACS).

A 'marker for chondrocyte phenotypic stability' as used herein refers to an mRNA or protein, the expression of which in a population is correlated to chondrocyte phenotypic stability, i.e. the ability of said cell population of producing hyaline cartilage (as detailed herein).

A 'ligand' for CXCR1 or CXCR2 as used herein refers to a molecule capable of activating the CXCR1 and/or CXCR2 receptors. Ligands for the CXCR1 and CXCR2 receptors are described in the art and include chemokines (CXCL1-8) and derivatives thereof as well as synthetic molecules such as but not limited to those presented in U.S. Pat. No. 6,515,001.

An 'inhibitor' of CXCR1 and/or 2 relates to a molecule capable of inhibiting the activation of the CXCR1 and or CXCR2 receptor. Such inhibitors include inhibitory antibodies (such as those commercially available from) and synthetic antagonists such as, but not limited to those described in U.S. Pat. No. 6,300,325, U.S. Pat. No. 6,548,499, U.S. Pat. No. 6,566,387.

A 'cartilage defect' as used herein relates to a defect which involves the destruction of cartilage (also referred to as a cartilage defect). Particular cartilage defects envisaged in the context of the present invention are joint surface defects. Joint surface defects can be the result of a physical injury to one or more joints or can be caused by genetic or environmental factors. Most frequently, but not exclusively, such a cartilage defect will occur in the knee and will be caused for instance by trauma, ligamentous instability, malalignment of the extremity, meniscectomy, failed aci or mosaicplasty procedures or primary osteochondritis dessecans. According to a particular embodiment of the present invention the joint surface defect occurs in the context of osteoarthritis (early osteoarthritis or unicompartimental osteochondral defects). A cartilage defect is referred to as an osteochondral defect when there is damage to articular cartilage and underlying (subchondral) bone. Usually, osteochondral defects appear on specific weight-bearing spots at the ends of the thighbone and shinbone and the back of the kneecap. Cartilage defects in the context of the present invention should also be understood to comprise those conditions where repair of cartilage and/or bone is required in the context of surgery such as, but not limited to, cosmetic surgery (e.g. nose, ear). Thus cartilage defects can occur anywhere in the body where cartilage formation is disrupted or where cartilage is damaged or non-existent due to a genetic defect, more particularly where cartilage is important for the structure or functioning of an organ (e.g. structures such as menisci, the ear, the nose, the larynx, the trachea, the bronchi, structures of the heart valves, part of the costae, synchondroses, entheses).

The present invention furthermore relates to the use of CXCL6 in the treatment and prevention of defects of joint-related tissues (e.g. menisci, ligaments) such as but not limited to meniscal tears, or meniscal degradation, ligamentous ruptures. This treatment can be a co-treatment with classical treatment in order to speed up or improve the healing process and the quality of repair. Additionally defects of other tissues with a similar fibro-cartilage structure, such as intervertebral discs, are considered within the scope of the present application.

The term 'gene' as used herein refers to any DNA sequence comprising several operably linked DNA fragments such as a promoter, a 5' untranslated region (the 5'UTR), a coding region (which may or may not code for a protein), and an untranslated 3' region (3'UTR) comprising a polyadenylation site. Typically in plant cells, the 5'UTR, the coding region and the 3'UTR are transcribed into an RNA of which, in the case of a protein encoding gene, the coding region is translated into a protein. A gene may include additional DNA fragments such as, for example, introns. "Foreign" referring to a gene or DNA sequence present in a cell in the context of this invention is used to indicate that the gene or DNA sequence is not naturally found in that genetic locus in the cell.

As used herein the term 'promoter' refers to a DNA region, a sequence of which is recognized (directly or indirectly) by a DNA-dependent RNA polymerase during initiation of transcription and which includes the transcription initiation site, binding sites for transcription initiation factors and RNA polymerase. The promoter may also comprise binding sites for other regulatory proteins, such as enhancers or inhibitors of transcription.

According to a particular embodiment of the invention CXCL6 is used as a medicament in combination with chondrogenic cells or chondrogenic precursor cells. Precursor cells of chondrogenic cells include stem cells, which can be obtained from different tissues including bone-marrow or umbellical cord. Particularly suited as chondrogenic precursor cells are skeletal precursor cells, such as those obtained from the synovial membrane which are capable of differentiating into cartilage producing cells, such as those described in WO 01/25402.

According to another aspect of the present invention cells expressing CXCL6 are used for the repair of cartilage or osteochondral defects. Optionally, the CXCL6 expressing cells are chondrogenic cells. Chondrogenic cells, for use in the context of the present invention, can be obtained by expansion of cells obtained from a small cartilage biopsy. CXCL6-expressing cells for use in the treatment and/or prevention of a chondral or osteochondral defect can be autologous (self) or allogeneic, which can be either from a family member (related) or from one or more unrelated donors. Such cells can be freshly isolated, cultivated or passaged.

Expression of CXCL6 can be monitored on an mRNA or protein level, using techniques described in the art. Expression or absence of expression can optionally be confirmed by comparing the expression of CXCL6 of a given cell population or cells with the expression of a positive control (e.g. a structural protein, such as beta-actin) and a negative control. Optionally, expression of CXCL6 can be quantified as a ratio of CXCL6 expression over expression of a negative marker for chondrocyte phenotypic stability, such as ALK-1 for chondrocytes (as described in WO 01/24833, incorporated herein by reference).

Alternatively, cells expressing CXCL6 can be obtained, or endogenous expression of CXCL6-expressing cells can be supplemented, by introduction of a sequence encoding CXCL6 under control of a suitable promoter. DNA sequences encoding CXCL6 have been described in the art, such as, but not limited to the DNA sequences described in U.S. Pat. No. 6,410,268. Suitable promoters for controlling the expression of a DNA sequence encoding CXCL6 have been is described in the art and include constitutive and inducible promoters. Different cell types can be used according to this aspect of the invention. Preferably, the cells to be used for the treatment or prevention of a cartilage or osteochondral defect are cells which are chondrogenic (such as chondrocytes) or which can develop into chondrogenic cells (precursor cells, stem cells). Introduction of foreign DNA into these cells has been described in the art (such as, for instance, by Eiges et al. (2001) Curr Biol 11, 514-518, and in U.S. Pat. No. 6,413, 511).

According to another aspect of the invention, CXCL6 production is stimulated endogenously in the joint, by administration of a compound capable of inducing CXCL6 production by CXCL6-producing cells. Preferably, this compound is a compound capable of inducing CXCL6 in chondrogenic cells such as chondrocytes. Compounds capable of inducing CXCL6 production in chondrocytes in vitro are described in the art and include IL-1beta, LPS and poly rI:rC. Alternative compounds capable of stimulating CXCL6 expression by chondrogenic cells can be identified by classical induction experiments. Chondrogenic or precursor cells incubated in the presence of one or more candidate compounds can be screened altered expression of CXCL6 (RT-PCR, antibody staining) and/or for morphological parameters (cell morphology, histological staining) or for molecular parameters (expression of markers by precursor cells positively or negatively associated with the chondrogenic capacity of precursor cells, or markers positively or negatively associated with the chondrocyte stability of mature chondrocytes after differentiation of precursor cells or maturation of chondrogenic cells). Similar screenings can be performed to assay the effect of compounds on CXCL6 expression in osteogenic cells. Hence the present invention provides a method to screen for compounds that modulate the chondrogenic and/or osteogenic potential of cells.

Alternatively, a reporter construct with the promoter of CXCL6 is operably linked with a reporter gene (such as luciferase, LacZ, Green Fluorescent Protein, chloramphenicol transferase). Upon administration of compounds, altered (lowered or increased) levels of expression of the reporter gene are identified. These reporter assays can be performed by in vitro in a transcription/translation assay or can be performed in vivo after transfection of the reporter construct in to any cell line, but preferably in a cell line or a cell population derived from connective tissue or from cartilage.

Both in vivo and in vitro assays allow the large scale screening of compound libraries for their effect on CXCL6 expression and cartilage and/or bone formation being associated therewith.

The use of compounds which downregulate the expression levels and/or activity of CXCL6 signalling have their application in the treatment of disorders being associated with hyperactivity or hyperproliferation of chondrocytes. These compounds can be identified with the above mentioned screening methods. Other suitable compounds for the downregulation of CXCL6 signalling include antisense RNA or double stranded RNA (RNAi) for CXL6 or one of its receptors, antibodies or antibody fragments against CXCL6 or against one of its receptors. Alternatively, soluble receptors can be used or parts of CXCL6 or parts of one of its receptors, which bind to either the ligand or the receptor and consequently disturb the ligand receptor interaction.

According to yet another aspect of the present invention, CXCL6 is used for the formation of bone and cartilage in vitro. This is of use in the production of autologous cartilage or bone transplants for reconstructive surgery. Cartilage-producing cells and/or precursors of cartilage-producing cells are cultivated in vitro optionally on a matrix or in a gel, in the presence of CXCL6 to form synthetic cartilage-like material that is implanted subsequently into the cartilage defect. Methods for in vitro cartilage and bone formation are described in the art (such as, but not limited to methods described in WO01/68811, WO97/18842, WO02/070030, U.S. Pat. No. 5,786,217, U.S. Pat. No. 5,723,331 and WO98/32333).

According to yet another aspect of the present invention, expression of CXCL6 can be used as a marker for the capacity of the expanded chondrogenic cells or cell populations to form stable hyaline cartilage in vivo and, optionally, to select phenotypically stable chondrocytes within the expanded cell population. Thus, according to the present invention, chondrogenic cells or cell populations, particularly chondrocyte cell populations, can be identified as capable of producing stable hyaline cartilage, based on whether or not CXCL6 is expressed by said cells or cell populations. Optionally, the identification can be done based on the presence of CXCL6 and one or more other markers. Additional markers can be either positive markers (i.e. markers positively associated with chondrocyte phenotypic stability) or negative markers (negatively associated with chondrocyte phenotypic stability, such as those disclosed in WO01/24833). Optionally, identification of the cells or cell population can be done based on a ratio of expression of CXCL6 over expression of a negative marker for chondrocyte phenotypic stability for that cell population (such as ALK-1 for a chondrocyte population). Preferably this ratio will be 2:1 or more, or more particularly 5:1 or more. The use of markers for chondrocyte phenotypic stability is of interest for a variety of applications including the quality control and selection of cell populations for use in the prevention or repair of osteochondral defects (such as in autologous cell transplantation (ACT)), monitoring the passage by passage cell expansion of chondrogenic cells, and for identifying culture conditions suitable for obtaining or maintaining chondrocyte phenotypic stability. Such applications and methods for using such a positive marker for chondrocyte phenotypic stability (e.g. in DNA arrays or DNA chips for routine detection) are described in WO01/24833.

According to yet another embodiment of the invention CXCL6 can be used to maintain the chondrocyte phenotypic stability of a chondrocyte cell population or can be used to restore the chondrocyte phenotypic stability by adding CXCL6 and restoring the signalling pathway to a cell population which has lost its chondrocyte phenotypic stability. According to the invention, administration of CXCL6 to cell cultivation media ensures that the cells will maintain their ability to produce stable hyaline cartilage in vivo.

Similarly, CXCL6 signalling was found to be essential for the differentiation of precursor cells into chondrocytes. Administration of CXCL6 to cell cultivation media will ensure the proper differentiation of precursor cells into chondrocytes. Alternatively, CXCL6 is used to restore the signalling pathway of chondrocyte precursor populations which have lost their capacity to differentiate into chondrocytes.

CXCL6 and/or CXCL6-producing cells and/or CXCL6-inducing compounds are, according to the present invention applied as a pharmaceutical composition in the treatment of cartilage or osteochondral defects. A pharmaceutical composition according to the present invention relates to a composition comprising CXCL6 and/or CXCL6-producing cells and/or CXCL6-inducing compounds, if required, with a suitable pharmaceutical carrier.

Optionally, the pharmaceutical composition of the present invention can further comprise compounds which promote the production of cartilage (and if necessary underlying bone), i.e. chondrogenic compounds, such as, but not limited to transforming growth factors and bone morphogenic proteins.

A suitable pharmaceutical carrier as used herein relates to a carrier suitable for medical or veterinary purposes, not being toxic or otherwise unacceptable. Such carriers are well known in the art and include saline, buffered saline, dextrose, water, glycerol, ethanol, and combinations thereof. The formulation should suit the mode of administration.

The therapeutic application of the present invention includes administering the composition comprising CXCL6 or CXCL6-producing cells locally as an application, injection, implant or device. When administered, the therapeutic composition for use in this invention is, preferably, in a pyrogen-free, physiologically acceptable form. Further, the composition may desirably be encapsulated or injected in a viscous form for delivery to the site of cartilage (and underlying bone) damage. Other therapeutically useful agents may also optionally be included in the composition as described above, may alternatively or additionally, be administered simultaneously or sequentially with the composition of the invention. Preferably for cartilage formation, the composition would include a matrix capable of delivering CXCL6 proteins to the site of cartilage damage.

As used herein the term matrix refers to a substrate which can be applied to a cartilage or osteochondral defect. Its function can be that of a 'carrier' of biomolecules, such as CXCL6 according to the present invention, but the matrix can also have a repair function in itself. Thus, according to one embodiment, its size and shape conforms to the cartilage or osteochondral defect such that the defect is repaired. The matrix can be configured as a sheet or a tapered shape. The matrix can be made up of any suitable material, including synthetic polymeric material and ground substances. Examples of matrices are the biodegradable and chemically defined calcium sulfate, tricalciumphosphate, hydroxyapatite, polylactic acid, polyglycolic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material. The matrix can also have an undefined shape and be of non-solid material or gel-like. Preferably, the matrix is bioresorbable. The matrix can be either cross-linked or not, depending on the application. Examples of matrices are described in U.S. Pat. No. 6,514,514, incorporated herein by reference. According to a particular embodiment of the present invention the matrix allows administration of CXCL6 in a gradient to the osteochondral defect, The gradient can correspond to the variable degree of repair needed in the defect and/or to the transition of cartilage (low concentration) to bone (high concentration). Gradients of CXCL6 can be applied for example by using matrices with a gradient in pore size. Filling such a matrix with a polymerisable solution with CXCL6 will result in a concentration gradient of CXCL6.

The therapeutic application of CXCL6 or CXCL5 inducing compounds according to the present invention also includes application by way of a delivery system, allowing controlled release. This can be achieved by selecting appropriate polymer carriers such as for example polyesters, polyamino-acids, polyvinyl-pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and other polymers, known to the person skilled in the art. Such methods include colloid drug delivery systems like liposomes, microspheres, microemulsions, nanoparticles, nanocapsules and so on.

Depending on the route of administration, the pharmaceutical composition comprising CXCL6 or CXCL6 inducing compounds of the invention may require protective coatings.

Therapy comprising the administration of CXCL6 may also be obtained by expression of CXCL6 in vivo, i.e. through gene therapy. Thus, for example, cells from a patient may be engineered with a polynucleotide (DNA or RNA) encoding a CXCL6 polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention. Alternatively, vectors (such as infectious viral particles or non-viral particles such as liposomes or micelles) comprising a DNA encoding CXCL6, can be used for the engineering of CXCL6-expressing cells in vivo, according to methods described in the art. The application of gene therapy in orthopaedics is described (review by Evans & Robbins (2000) *Orthop Nurs* 19, 16-22), and methods of gene therapy using CXCL6 are found in U.S. Pat. No. 6,410,268. According to a preferred embodiment of the present invention, cells engineered for the expression of CXCL6, or vectors for the introduction of DNA in vivo, are administered locally to the environment of the cartilage or osteochondral defect to be treated.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides or cells of the present invention may be employed in conjunction with other therapeutic compounds.

As used herein "comprising" is to be interpreted as specifying the presence of the stated features, integers, steps, reagents or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA sequence which is functionally or structurally defined, may comprise additional DNA sequences, etc.

BRIEF DESCRIPTION OF THE FIGURES

The following Examples, not intended to limit the invention to specific embodiments described, may be understood in conjunction with the accompanying Figures, incorporated herein by reference, in which.

EXAMPLES

Example 1

Involvement of Chemokines in the Differentiation of Human Mesenchymal Stem Cells (MSCs)

It has been described that human MSCsderived from bone marrow can be stimulated to differentiate into cartilage producing cells by TGFbeta (Mackay et al. (1998) *Tissue Eng* 4, 41-28). To assess the involvement of CXC chemokines in this differentiation process, micromass pellets of mesenchymal stem cells obtained from synovial membrane were plated in medium containing 10% heat inactivated serum. After 3 hours 485 microliter of SF medium was added. The next day the SF medium was refreshed and the antibodies and growth factors were added in 100× solutions (5 µl/well): either TGF-beta (5 ng/ml), antibodies to CXCR1 or CXCR2 (final concentration of 5 g/ml), or soluble CXCR1 and 2. The capacity to produce cartilage by these cells was measured by whole mount alcian blue staining of the micromass and detection of staining at O.D. The results are provided in FIG. 1.

Figure 1:
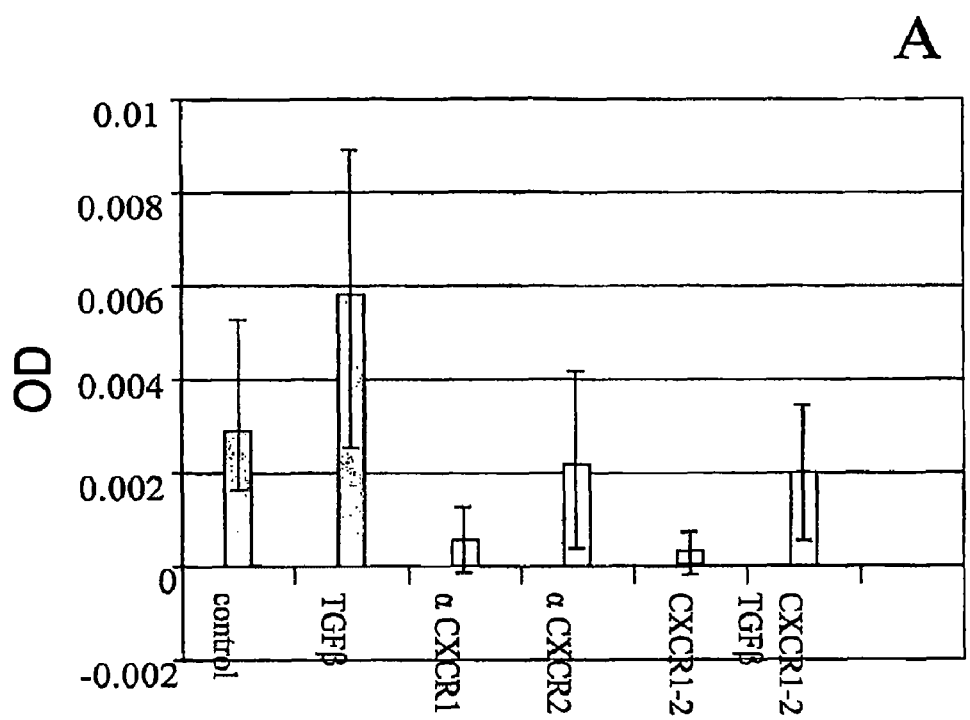
FIG. 1: Effect of blocking of the CXC-chemokine pathway on the differentiation of hMSCs into chondrogenic cells. Incubation of the cells without additives (control) or with TGFbeta, antibodies to the CXCR1 or CXCR2 receptor (αCXCR1, αCXCR2), soluble CXCR1 and CXCR2 receptor (CXCR1-2) or soluble receptor+TGFbeta. Y-axis represents OD measured from the alcian blue staining of whole mount micromasses indicative for cartilage formation.

As can be seen from FIG. 1, there is some spontaneous differentiation of stem cells into cartilage-producing cells in the absence of added growth factors, but this is greatly enhanced by addition of TGFbeta. Addition of antibodies against CXCR1, and to a lesser extent antibodies to CXCR2, inhibited the spontaneous differentiation into chondrogenic cells, while addition of soluble CXCR1 and 2 receptor inhibited the TGFbeta-induced differentiation. Moreover it was found that addition of CXCL6 (100 ng/ml) together with the antibodies to CXCR1 or 2 restored differentiation, suggesting that there is a competition between CXCL6 and the antibodies for the receptor. These data indicate the involvement of CXC-chemokines on differentiation of mesenchymal stem cells into chondrogenic cells.

Example 2

Expression of CXCL6 in Cell Populations which are Phenotypically Stable

Three pools of human articular chondrocytes were obtained from articular cartilage from human donors not having suffered from any articular disease. Briefly, cartilage was sliced full thickness placed in Hank's Balanced Salt Solution ("HBSS") (available from Life Technologies) supplemented with penicillin, streptomycin, and amphotericin B (Life Technologies). After two washes in HBSS during 5 minutes at 37° C., cartilage was finely minced and placed in a sterile 0.2% crude collagenase (Life Technologies) solution in Dulbecco's Modified Eagle Medium ("DMEM") with high glucose (Life Technologies) containing 10% FBS (Biowittaker), penicillin, streptomycin, and amphotericin B. After overnight incubation at 37° C., cells were washed twice in culture medium—DMEM supplemented with 10% FBS, 100 units/ml penicillin, 100 µg/ml of streptomycin, and 0.25 µg/ml of amphotericin B—and counted with trypan-blue exclusion test to adjust for the number of viable cells. The resulting cells were cultured in monolayer. Upon the first passage (P0), 2 aliquots ($5 \times 10^6$ cells each) were injected in an in vivo for chondrocyte stability as described in WO 01/24833. A smaller aliquot was used to obtain the RNA extract and the rest was re-plated. Total RNAs were reverse-transcribed using Thermoscript (available from Life Technologies) and used for semi-quantitative PCR analysis. After passage 5, two samples were placed in low melting-agarose cultures, a system known to result in a rescue of type II collagen expression by de-differentiated chondrocytes. After 2 months, colony formation was abundant and cultures were harvested for RNA extraction. Semi-quantitative RT-PCR analysis was carried out for expression of CXCL6.

Micro array analysis revealed that CXCL6 is expressed in freshly isolated (FI) chondrocytes and cultivated chondrocytes at P0. CXCL6 was down-regulated when these cells, after a number of passages, lost their capacity of cartilage formation in a nude mouse model. Thus, expression of CXCL6 by chondrogenic cells is linked to the ability to form hyaline cartilage.

Example 3

Animal Model of CXCL6-Induced Osteochondral Repair

The objective of this experiment was to demonstrate the effect of a CXCL6 in the repair of large osteochondral defects.

Animals: 7 Adult female non-lactating and not pregnant Saanen goats were used (4 treatments-3 controls). All goats were 2 years or older and derived from CAE (Caprine Arthritis and Encephalitis Virus)-negative certified farms.

Experimental Design

After a pre-anesthetic examination, and premedication (Xylazine 0.2 mg/kg+Atropine 0.02 mg/kg IM, antibiotics: Ampicillin 10 mg/kg, and pain medication: Fentanyl 0.1 mg/kg IM) goats were put under general anesthesia using Ketamine (2 mg/kg) and Midazolam (0.5 mg/kg). General aesthesia was maintained by inhalation anesthesia with Isoflurane and oxygen. Animals were monitored by ECG and MAP and received a venous infusion line with NaCl 0.9%.

A 6×6 mm osteochondral defect was made in the central part of the left medial femoral condyle. The defect was made as follows:

right dorsolateral decubitus, left leg hanging free in flexion.
routine clipping, disinfections and draping of left stifle region.
Skin incision of +/−7 cm immediately medial of patellar ligament.
Straight medial approach to the knee, small arthrotomy medially next to patellar ligament, removal of part of the Hoffa fat pad.
A 6 mm deep osteochondral defect is made in the central part of the medial femoral condyle using a 6 mm burr.
The defect is dried with a gauze swab.

The bony defect was filled with a piece of resorbable gelatin sponge (Spongostan™—0.6 cm×0.6 cm×0.6 cm—saturated with PBS) that served as a carrier. All defects were sealed with a periostal flap sutured on the cartilage. In the animals of the experimental group, 80-100 µl of human CXCL6 (0.025 µg/µl, R&D Systems, Europe) was injected under the flap and absorbed by the gelatin sponge. Nothing was injected in the controls.

The wound was closed in 4 layers and the leg was immobilized in a sling bandage.

Further treatment with Fentanyl 0.1 mg/kg IM was provided postoperatively as necessary.

Animals were kept in the sling bandage during 3 weeks (no weight bearing possible), after which free movement was allowed. Clinical evaluation and wound care were performed daily. Skin sutures were removed 2 weeks post-operatively. Until sacrifice, the animals were housed individually in small cages (1.1 m×1.8 m).

Animals were sacrificed 13 weeks post-op., unless complications occurred that required euthanasia on humane grounds. Goats were euthanized by an intravenous injection of T61 (0.1 ml/kg). After removal of the skin, synovial fluid was collected from both operated and contralateral stifle joints in a sterile way. Left and right stifles were excised and preserved in formaldehyde. A synovial biopsy was performed on both stifle joints, which were also preserved in formaldehyde.

Clinical Evaluations, Laboratory Tests and Follow Up

Pre-operatively and at time of sacrifice, blood and urine samples were taken. Blood samples were tested for multiple factors (Hb, Hct, RBC, MCV, MCH, MCHC, RDW, WBC+formula, eosin. Count, Thromb. Ret., Fe, Fibrinogen+TP/Fibr. Ratio, Na, K, Cl, Ca, PO4, Mg, Ureum, TP+electrophoresis, AST, GGT, AP, LDH). Urine was tested for presence of red blood cells and protein. Synovial fluid upon sacrifice was checked by cell count, TP, crystals, bacteriology Criteria of Evaluation Before sacrifice the joints of the animals were evaluated for muscle atrophy, gait analysis at walk.

Evaluation of repair of the chondral defect was based on both an optical and histological analysis of the synovial biopsy. Histological analysis of the synovial fluid was done by H&E-staining, of the condyles by H&E-staining, Toluidine Blue staining and Saffranin 0-staining.

Figure 2:
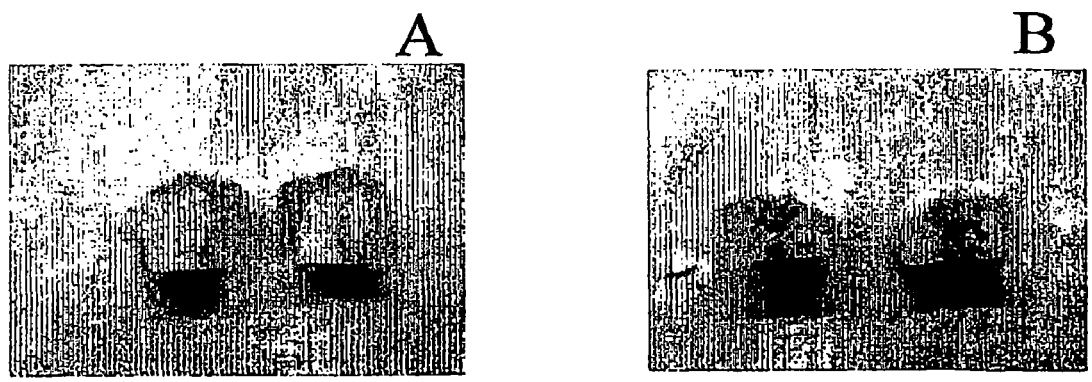
FIG. 2: Macroscopic cross-section of the osteochondral defect zone of control in (A) and CXCL6-treated in (B)
Figure 3:
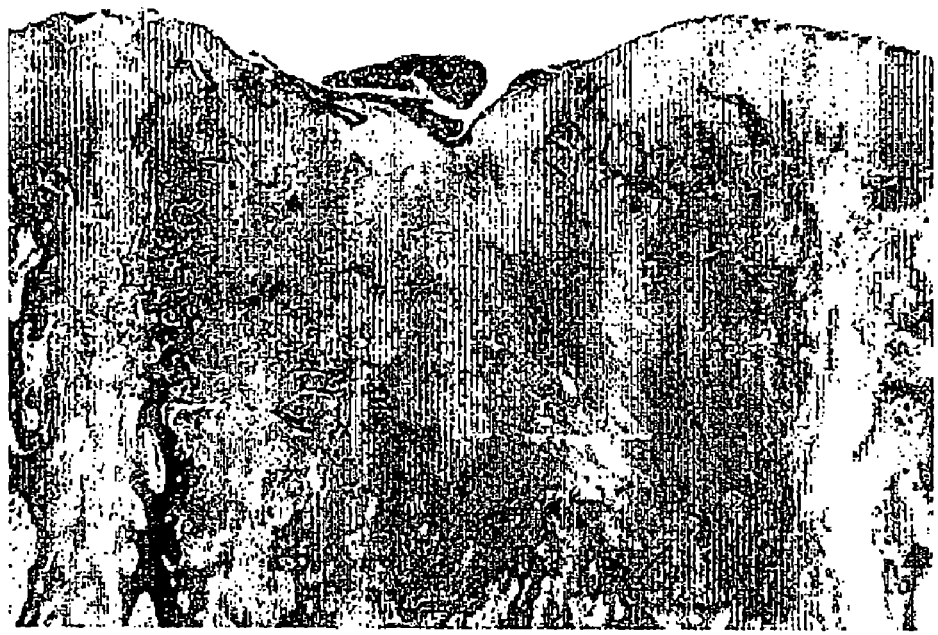
FIG. 3: Overview of longitudinal section of osteochondral defect zone after HE staining. (A) control, (B) CXCL6-treated
Figure 3:
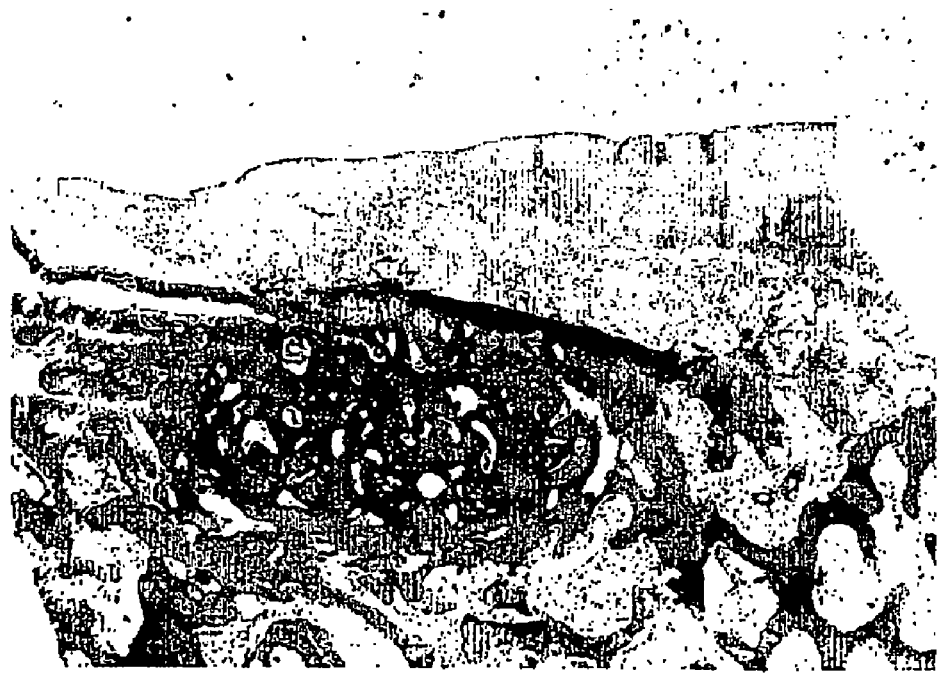

Histological stains were blindly evaluated and scored. The following criteria were used:
tissue morphology (type of cartilage, if any)
presence of Inflammation
Structural integrity (presence of columnar organization)
Chondrocyte clustering
Formation of tidemark
Subchondral bone formation
Architecture of surface
Lateral integration (whether or not bonded at one or both ends of graft)
Basal integration Results:

FIGS. 2 and 3 demonstrate the difference in repair occurring in CXCL6-treated knees as compared to defects to which CXCL6 was not added. It can be seen that, in the absence of CXCL6, the joint defect zone is vascularized and consists mainly of fibro-cartilage. In the CXCL6 treated defect there is a repair of hyaline cartilage and underlying bone. An overview of the evaluation criteria for a joint defect treated with CXCL6 and one not treated with CXCL6 is provided in Table 2.

TABLE 2

| Criteria | Osteochondral defect + Spongostan + periost | Osteochondral defect + Spongostan + periost + chemokine |
| --- | --- | --- |
| Tissue morphology | Mostly fibrocartilage | Mostly hyaline cartilage |
| Structural integrity | Beginning of columnar organization | Beginning of columnar organization |
| Chondrodycte clustering | No clusters | No clusters |
| Formation of tide-mark | <25% | 76-90% |
| Subchondral bone formation | None | Good |
| Architecture of the surface | Slight fibrillation or irregularity | Normal |
| Lateral integration | Bonded at one end | Bonded at both ends of graft |

TABLE 2-continued

| Criteria | Osteochondral defect + Spongostan + periost | Osteochondral defect + Spongostan + periost + chemokine |
|---|---|---|
| Basal integration | 91-100% | 91-100% |
| Inflammation | none | None |

In the biopsy of a joint defect to which CXCL6 had been added, an almost complete filling of the bone defect with newly formed subchondral bone and hyaline-like to hyaline cartilage on top was observed. The cartilage layer was thinner than the surrounding cartilage because of moving up of the bone front. In controls, the defect was filled with mixed tissue, consisting of the collagen carrier, cartilage, fibrous tissue, blood vessels and some bone.

The invention claimed is:

1. An in vitro method of inducing or restoring differentiation of a mesenchymal stem cell population into chondrocytes, said method comprising the step of administering CXCL6 (chemokine with CXC motif, ligand 6) protein in vitro to said mesenchymal stem cell population, thereby inducing or restoring differentiation of the mesenchymal stem cell population into chondrocytes.

2. The method according to claim 1, wherein said mesenchymal stem cells are obtained from bone marrow, umbilical cord or synovial membrane.

* * * * *

UNITED STATES PATENT AND TRADEMARK OFFICE
CERTIFICATE OF CORRECTION

PATENT NO. : 7,842,502 B2  Page 1 of 1
APPLICATION NO. : 12/345369
DATED : November 30, 2010
INVENTOR(S) : Frank Luyten et al.

It is certified that error appears in the above-identified patent and that said Letters Patent is hereby corrected as shown below:

Column 2, Line 56, replace "*Left.*" with --*Lett.*--.

Column 6, Line 24, replace "cystein" with --cysteine--.

Column 8, Lines 7-8, replace "methods is known" with --methods known--;

Line 41, replace "unicompartimental" with --unicompartmental--.

Column 10, Line 52, replace "CXL6" with --CXCL6--.

Signed and Sealed this
Twenty-fifth Day of December, 2012

David J. Kappos
*Director of the United States Patent and Trademark Office*